United States Patent
Takanashi et al.

(10) Patent No.: US 9,244,076 B2
(45) Date of Patent: Jan. 26, 2016

(54) FLUORESCENT LABEL FOR BIOLOGICAL SUBSTANCE DETECTION METHOD

(71) Applicant: Konica Minolta, Inc., Tokyo (JP)

(72) Inventors: Kensaku Takanashi, Tokyo (JP); Hisatake Okada, Tokyo (JP); Yasushi Nakano, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 98 days.

(21) Appl. No.: 14/200,139

(22) Filed: Mar. 7, 2014

(65) Prior Publication Data

US 2014/0186857 A1 Jul. 3, 2014

Related U.S. Application Data

(63) Continuation-in-part of application No. PCT/JP2012/072496, filed on Sep. 4, 2012.

(30) Foreign Application Priority Data

Sep. 9, 2011 (JP) .................. 2011-197339

(51) Int. Cl.
*A61K 9/14* (2006.01)
*G01N 33/58* (2006.01)
(Continued)

(52) U.S. Cl.
CPC .......... *G01N 33/582* (2013.01); *G01N 21/6428* (2013.01); *G01N 33/56966* (2013.01); *G01N 33/57492* (2013.01); *G01N 2021/6439* (2013.01)

(58) Field of Classification Search
CPC .................................................. G01N 33/582
See application file for complete search history.

(56) References Cited

U.S. PATENT DOCUMENTS 5,093,147 A * 3/1992 Andrus et al. .................. 427/7
5,304,645 A 4/1994 Klein et al.
(Continued)

FOREIGN PATENT DOCUMENTS

EP 2755026 7/2014
EP 2757378 7/2014
(Continued)

OTHER PUBLICATIONS

Zhu, Reversibly Photoswitchable Dual-Color Fluorescent Nanoparticle as new Tools for Live-Cell Imaging, J. Am. Chem. Soc., 2007, 129, 3524-3526.*
(Continued)

*Primary Examiner* — Paul Dickinson
(74) *Attorney, Agent, or Firm* — Lucas & Mercanti, LLP

(57) ABSTRACT

The present invention provides a fluorescent label that can be used for carrying out a biological substance detection method for specifically detecting a biological substance from a pathological specimen, by which method, when immunostaining using a fluorescent label and staining for morphological observation using a staining agent for morphological observation are simultaneously performed, the results of fluorescence observation and immunostaining can be assessed properly even if the fluorescent label and/or the staining agent is/are deteriorated by irradiation with an excitation light. The fluorescent label is a fluorescent dye-containing nanoparticle in which the parent material is a cross-linked polymer and the fluorescent dye is an aromatic ring-based dye molecule. The cross-linked polymer is suitably a melamine resin or a styrene resin. The aromatic ring-based dye molecule is suitably a perylene and more suitably a perylene diimide. The dye molecule can have a polar group such as sulfonic acid group or its acid halide.

5 Claims, 2 Drawing Sheets

(51) Int. Cl.
*G01N 21/64* (2006.01)
*G01N 33/569* (2006.01)
*G01N 33/574* (2006.01)

(56) References Cited

U.S. PATENT DOCUMENTS

| | | | |
|---|---|---|---|
| 5,995,645 | A | 11/1999 | Soenksen et al. |
| 2008/0032328 | A1 | 2/2008 | Cline et al. |
| 2008/0193758 | A1 | 8/2008 | Kuebelbeck |
| 2010/0035365 | A1 | 2/2010 | Wiesner et al. |
| 2010/0084610 | A1* | 4/2010 | Iftime et al. ............. 252/301.35 |
| 2013/0157287 | A1 | 6/2013 | Takanashi et al. |
| 2013/0157895 | A1 | 6/2013 | Aimiya et al. |
| 2014/0186857 | A1 | 7/2014 | Takanashi et al. |
| 2014/0212889 | A1 | 7/2014 | Gouda et al. |

FOREIGN PATENT DOCUMENTS

| | | |
|---|---|---|
| JP | 62174067 | 7/1987 |
| JP | S62-174067 A | 7/1987 |
| JP | 05-150164 A | 6/1993 |
| JP | H06-160387 | 6/1994 |
| JP | 08-320437 A | 12/1996 |
| JP | 2001-525580 A | 12/2001 |
| JP | 2007-029032 A | 2/2007 |
| JP | 2008-147394 A | 6/2008 |
| JP | 2008-543982 | 12/2008 |
| JP | 2009-014939 A | 1/2009 |
| JP | 2009-115599 A | 5/2009 |
| JP | 2010-134195 A | 6/2010 |
| JP | 2010-209314 A | 9/2010 |
| JP | 2010-229219 | 10/2010 |
| JP | 2010-261791 | 11/2010 |
| WO | WO 2008/006006 | 1/2008 |
| WO | WO 2011022141 A1 * | 2/2011 |
| WO | 2012/029342 | 3/2012 |
| WO | 2012/029752 | 3/2012 |

OTHER PUBLICATIONS

Extended European Search Report dated May 19, 2015 from the corresponding European Patent Application No. 12829813.0.
Tuominen Vilppu J et al: "ImmunoRatio: a publicly available web application for quantitative image analysis of estrogen receptor (ER), progesterone receptor (PR), and Ki-67", Breast Cancer Research, Curren Science, London, GB, vol. 12, No. 4, Jul. 27, 2010, p. R56.
Japanese Office Action, Japanese Application 2014-035295. Issuance date: Jul. 1, 2014 (2 pages) and English translation (2 pages).
Article: Linyong Zhu, Reversibly Photoswitchable Dual-Color Fluorescent Nanoparticles as New Tools for Live-Cell Imaging, Journal of the American Chemical Society, Mar. 28, 2007, vol. 129/Iss. 12, 3524-3526. (3 pages).
Office Action for corresponding Japanese patent application No. 2014-035295 dated Jan. 6, 2015 and English translation thereof.
The extended European Search Report dated Jul. 21, 2015 issued from the corresponding European Patent Application No. 14163828.8.

* cited by examiner

FLUORESCENT LABEL FOR BIOLOGICAL SUBSTANCE DETECTION METHOD

This is a continuation-in-part of PCT/JP2012/072496 filed Sep. 4, 2012, which claimed the priority of Japanese Patent Application No. 2011-197339 filed Sep. 9, 2011, the priority of both applications are claimed and both applications are incorporated herein by reference.

TECHNICAL FIELD

The present invention relates to a biological substance detection method. More particularly, the present invention relates to tissue staining in which a tissue is stained with a fluorescent label.

BACKGROUND ART

As a medical diagnosis, a pathological diagnosis is performed. A pathologist diagnoses a disease using a tissue section collected from a human body and informs a clinician of whether or not a therapy and/or a surgery is/are necessary. Based on the patient conditions and pathological diagnosis, a physician determines pharmacotherapeutic strategies and a surgeon determines whether or not a surgery should be performed.

In pathological diagnosis, it is a common practice to prepare a tissue sample by slicing a tissue specimen obtained by evisceration or needle biopsy into a thickness of several micrometers or so and observe the tissue sample at a magnification under a light microscope so as to obtain various findings. In many cases, a specimen is prepared by fixing a collected tissue through dehydration and paraffin blocking, slicing the resultant into a thickness of several micrometers and then removing the paraffin. Here, since the specimen hardly absorbs or scatters any light and is thus nearly colorless and transparent, it is usually stained with a dye prior to being observed.

There have been proposed a variety of staining techniques. In particular, for tissue samples, hematoxylin-eosin staining (HE staining) using two dyes, hematoxylin and eosin, is typically used as staining for observing the morphology of a specimen (Patent Literatures 1 and 2). Hematoxylin stains cell nuclei, calcareous parts, cartilaginous tissues, bacteria and mucus in livid to light blue, while eosin stains cytoplasm, interstitial tissues, various fibers, erythrocytes and keratinocyte in red to dark red. A pathologist makes a diagnosis based on morphological information and staining information, such as changes in the size and shape of cell nuclei and changes in the pattern as a tissue, in a microscope image of a stained tissue sample. Examples of other staining for morphological observation include Papanicolaou staining (Pap staining) used for cytological diagnosis.

Further, in pathological diagnosis, immunological observation in which molecular target staining called immunostaining is performed for confirming the expression of molecular information of a specimen and functional abnormalities such as abnormal expression of a gene or a protein are diagnosed is performed. For immunostaining, for example, a dye staining method using an enzyme (DAB staining) is employed. In DAB staining, an antibody modified with peroxidase, which is capable of allowing DAB (diaminobenzidine) as a substrate to show a color, is used to stain an antigen to be observed with the color and the amount of the antigen is determined by observing the stained antigen. Alternatively, fluorescent labeling may be employed. In fluorescent labeling, the amount of the subject antigen is determined by staining the antigen with an antibody modified with a fluorescent dye and observing the stained antigen.

At present, attempts are being made to simultaneously perform morphological observation and immunological observation of a specimen and, for example, it has been tried to simultaneously perform HE staining for morphological observation and DAB staining for immunological observation (Patent Literature 3). However, since staining with an enzyme label, such as DAB staining, develops a color similar to the color developed by HE staining and the colors developed by HE staining and staining with an enzyme label cannot thus be easily distinguished, there is a problem that such simultaneous observation is difficult. In addition, in DAB staining, since the staining concentration is largely affected by the environmental conditions such as temperature and time, there is a problem that estimation of the actual amount of an antibody or the like from the staining concentration is difficult.

On another front, in pathological diagnosis, fluorescent labeling using a fluorescent label is also performed. This method characteristically has excellent quantitative capability as compared to DAB staining. In cases where pathological diagnosis and morphological observation are simultaneously performed using a fluorescent label, there is a problem that the results are likely to be affected by the fluorescence of the staining agent used for tissue staining. As a countermeasure, for example, a fluorescent dye which has peaks of excitation and emission wavelengths in the infrared region and is thus not likely to be affected by visible light can be used (Patent Literature 4). Alternatively, for example, the excitation and emission wavelengths of a staining agent for morphological observation and those of a fluorescent label for immunostaining can be shifted.

Meanwhile, it is known that dyes are easily deteriorated generally in the short-wavelength side, particularly in the ultraviolet region. Considering the effect on deterioration of a staining agent and a fluorescent label, it is desired that they be excited in the visible region rather than in the ultraviolet region.

As fluorescent labels, dyes, inorganic nanoparticles (that may also be referred to as "semiconductor nanoparticle", "quantum dot" or the like) and aggregates thereof are known to be utilized (Patent Document 5). Thereamong, inorganic nanoparticles are not suitable as the above-described fluorescent label to be excited in the visible region; therefore, it is difficult to utilize inorganic nanoparticles. On the other hand, fluorescent dyes and aggregates thereof can be utilized as the above-described fluorescent label to be excited in the visible region. It has been reported that, between a fluorescent dye and an aggregate thereof, the light-resistant performance is more improved by the latter (Patent Document 6). Furthermore, between a dye and an aggregate thereof, the brightness of individual dye is higher in the aggregate.

CITATION LIST

Patent Literatures

[Patent Literature 1] JP 2001-525580 A
[Patent Literature 2] JP 2009-115599 A
[Patent Literature 3] JP 2010-134195 A
[Patent Literature 4] WO 2008/006006
[Patent Literature 5] JP 2010-209314 A
[Patent Literature 6] JP 2008-147394 A

SUMMARY OF INVENTION

Technical Problem

In cases where pathological diagnosis and morphological observation are simultaneously performed using the above-described fluorescent label, a confocal laser microscope or a fluorescence microscope is used for observation of the fluorescent label. In fluorescence observation under these microscopes, a stained section is irradiated with a high-intensity excitation light. This excitation light gradually deteriorates fluorescent labels using a fluorescent dye or the like and staining agents such as eosin and this has a great effect in fluorescence observation and assessment of immunostaining results. Ideally, neither of a fluorescent label nor a staining agent is deteriorated; however, the reality is that they are deteriorated at a certain rate.

In view of the above, a main object of the present invention is to provide a fluorescent label that can be used for carrying out a method by which the results of fluorescence observation and immunostaining can be assessed properly even when a fluorescent label and/or a staining agent is/are deteriorated by irradiation with an excitation light as described above.

Solution to Problem

The present inventors discovered a biological substance detection method for specifically detecting a biological substance from a pathological specimen, in which method, in cases where immunostaining using a fluorescent label (particularly a fluorescent dye-containing nanoparticle) and staining for morphological observation using a staining agent for morphological observation are simultaneously performed, assessments of the results of fluorescence observation and immunostaining are hardly affected when the fluorescent label used for immunostaining is observed and the brightness retention rate (ratio of the brightness at the time of the observation with respect to the brightness at the initiation of irradiation with an excitation light) of an immunostained part (sites that are immunostained with the fluorescent label) is found to be in a range of 80% to 120% in relation to the brightness retention rate of a part stained for morphological observation (sites that are not immunostained with the fluorescent label but stained with the staining agent for morphological observation). Further, the present inventors discovered that a fluorescent label comprising a fluorescent dye-containing nanoparticle in which the parent material is a cross-linked polymer and the fluorescent dye is an aromatic ring-based dye molecule is suitable for carrying out such a biological substance detection method.

That is, the present invention encompasses the followings.
[1] A fluorescent label comprising a fluorescent dye-containing nanoparticle characterized in that the parent material is a cross-linked polymer and the fluorescent dye is an aromatic ring-based dye-molecule.
[2] The fluorescent label according to [1], wherein the above-described cross-linked polymer is a melamine resin.
[3] The fluorescent label according to [1], wherein the above-described cross-linked polymer is a styrene resin.
[4] The fluorescent label according to [1], wherein the above-described aromatic ring-based dye molecule is a perylene.
[5] The fluorescent label according to [4], wherein the above-described perylene is a perylene diimide.
[6] The fluorescent label according to [1], wherein the above-described aromatic ring-based dye molecule has a polar group.
[7] The fluorescent label according to [6], wherein the above-described polar group is sulfonic acid group or its acid halide.
[8] The fluorescent label according to [1], wherein the above-described aromatic ring-based dye molecule has a maximum excitation wavelength in a wavelength range of 550 nm to 620 nm and maximum emission wavelength is in a wavelength range of 580 to 700 nm.
[9] The fluorescent label according to [1], wherein the average particle diameter of the above-described fluorescent dye-containing nanoparticle is 50 to 200 nm.

Advantageous Effects of Invention

According to the fluorescent label of the present invention, a biological substance detection method in which the results of fluorescence observation and immunostaining can be assessed properly even when the fluorescent label and/or a staining agent is deteriorated can be carried out.

DESCRIPTION OF EMBODIMENTS

Figure 1:
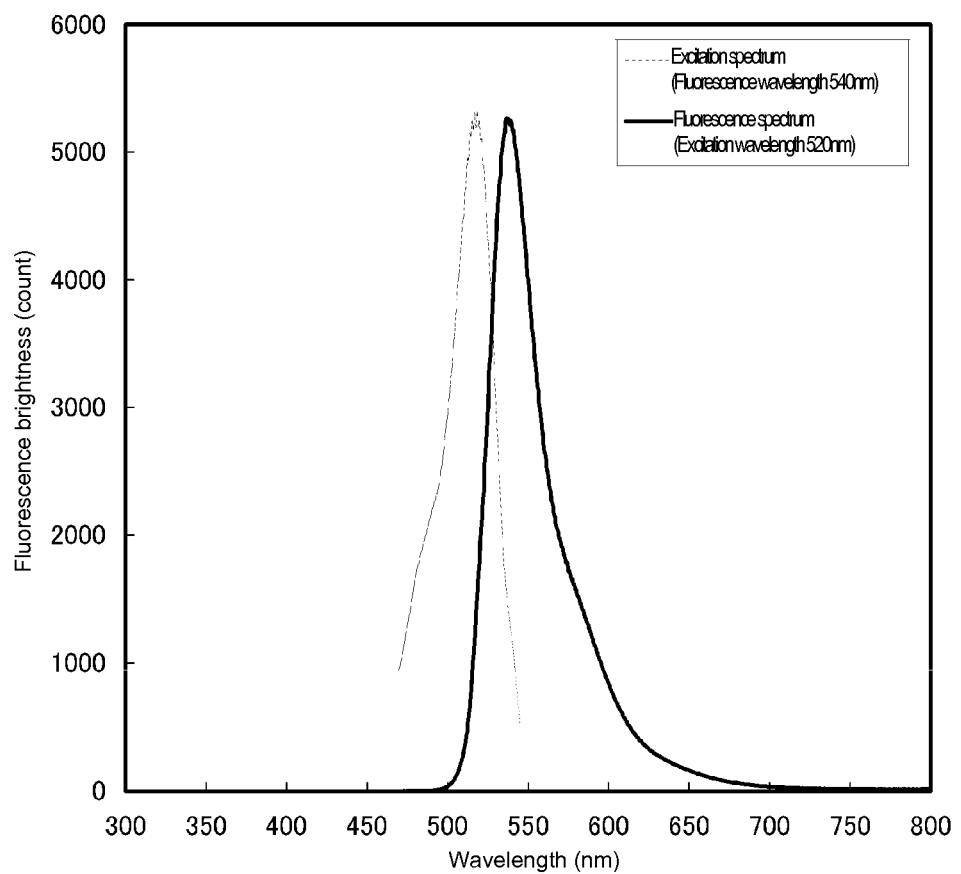
FIG. 1 shows the fluorescence spectrum (excitation wavelength=520 nm) and the excitation spectrum (fluorescence wavelength=540 nm) of eosin.

The mode for carrying out the invention will now be described; however, the present invention is not restricted thereto.

The biological substance detection method according to a typical embodiment of the present invention is a method of specifically detecting a biological substance from a pathological specimen, which basically comprises: (1) the step of immunostaining a pathological specimen with a fluorescent label; (2) the step of staining the pathological specimen for morphological observation with a staining agent for morphological observation; and (3) the step of irradiating the thus stained pathological specimen with an excitation light to allow fluorescence to be emitted for detection of a biological substance from the pathological specimen. In addition, the biological substance detection method may also comprise a deparaffinization step, an activation treatment step and/or the like in the same manner as in an ordinary biological substance detection method.

In the present invention, particularly in (1) the step of immunostaining a pathological specimen, it is expected that, as the fluorescent label, a fluorescent dye-containing nanoparticle whose excitation wavelength is in a range different from the excitation wavelength range of a staining agent for morphological observation will be employed. However, in the present invention, the fluorescent label for immunostaining is not restricted to such a fluorescent dye-containing nanoparticle and it is also possible to use other fluorescent label which can satisfy a condition that, when observed, the brightness retention rate of an immunostained part is in a range of 80% to 120% in relation to the brightness retention rate of a part stained for morphological observation.

It is noted here that whichever (1) the step of immunostaining or (2) the step of staining for morphological observation may be performed first and the order (sequence) of these steps is not a matter of importance. Regardless of the order of the immunostaining and the staining for morphological observation, "immunostaining using a fluorescent label and staining for morphological observation using a staining agent for morphological observation are simultaneously performed".

The details of the staining agent for morphological observation, the fluorescent label for immunostaining (fluorescent dye-containing nanoparticle), the staining for morphological observation, the immunostaining and the like will now be described below.

[Staining Agent for Morphological Observation]

As the staining agent for morphological observation, hematoxylin and eosin are particularly suitably used; however, the staining agent for morphological observation is not restricted thereto. Any dye may be used as long as it is capable of staining cytoplasm and the like in the same manner as eosin and has excitation and emission wavelengths that are similar to those of eosin in the visible region. For example, orange G, eosin Y and light green SFY, which are used in Papanicolaou staining (Pap staining) performed for cytological diagnosis, are also dyes having excitation and emission wavelengths that are similar to those of eosin in the visible region. As for hematoxylin as well, any dye may be used as long as it is capable of staining cell nuclei in the same manner as hematoxylin and has excitation and emission wavelengths that are similar to those of hematoxylin in the visible region.

[Fluorescent Label for Immunostaining]

In the present invention, the fluorescent label for immunostaining is one which can achieve a condition that, when the fluorescent label used for immunostaining is observed, the brightness retention rate of an immunostained part is in a range of 80% to 120% in relation to the brightness retention rate of a part stained for morphological observation. That is, as the fluorescent label for immunostaining, one whose reduction in the brightness retention rate caused by irradiation with an excitation light can be synchronized within a certain range with a reduction in the brightness retention rate of a staining agent for morphological observation (which is represented by hematoxylin and eosin) to be used in combination is employed.

Further, eosin used in HE staining, which is one of the staining techniques used for morphological observation, emits fluorescence depending on the microscopy conditions. Since the absorption wavelength of eosin overlaps with the excitation wavelengths of many fluorescent labels, the fluorescence emitted by eosin used in the staining may potentially interfere with the observation of a fluorescent label. The fluorescence spectrum (excitation wavelength=520 nm) and the excitation spectrum (fluorescence wavelength=540 nm) of eosin are shown in FIG. 1. From the excitation spectrum, it is seen that eosin is efficiently excited in a wavelength range of longer than 450 nm to shorter than 550 nm. Therefore, in the present invention, it is preferred that the fluorescent label for immunostaining be one which has a maximum excitation wavelength outside this wavelength range, that is, in either a wavelength range of 350 to 450 nm or a long wavelength range of 550 nm or longer. It is noted here, however, that the maximum excitation wavelength is more preferably 620 nm or shorter, considering the balance with the fluorescence wavelength. From the standpoint of reducing the effect of excitation light on the staining agent as much as possible, it is more preferred to use a fluorescent label having a maximum excitation wavelength in a wavelength range of 550 to 620 nm than using a fluorescent label having a maximum excitation wavelength in a wavelength range of 350 to 450 nm. Meanwhile, considering the balance with the effects of absorption and emission by eosin and the tissue intrinsic fluorescence, it is preferred that the fluorescent label have a maximum emission wavelength in the long-wavelength side of 580 nm or longer. Further, since the fluorescent label is required to be visually confirmable when observed under a fluorescence microscope, it is also preferred that the fluorescent label have a maximum emission wavelength in the short-wavelength side of 700 nm or shorter.

[Fluorescent Dye-Containing Nanoparticle]

From the standpoint of the ratio of the signal value against the fluorescence of eosin and the intrinsic fluorescence of cells, which are noises, the higher the brightness of the fluorescent label, the more preferred it is. Therefore, in the present invention, a fluorescent dye-containing nanoparticle having a higher brightness than a fluorescent dye is suitably used as the fluorescent label.

The term "fluorescent dye-containing nanoparticle" refers to a nano-sized particle having a structure in which plural fluorescent dyes are encapsulated in a particle (parent material) made of an organic or inorganic material. The fluorescent dye-containing nanoparticle used in the present invention can be prepared by a known method by selecting, as raw materials, fluorescent dyes suitable for controlling the brightness retention rate of an immunostained part to be in a range of 80% to 120% in relation to the brightness retention rate of a part stained for morphological observation as well as an organic or inorganic material for forming a particle.

Examples of the organic or inorganic material for forming a particle include those into which fluorescent dyes can be encapsulated, such as polystyrene, polyamide, polylactic acid, polyacrylonitrile, polyglycidyl methacrylate, polymelamine, polyurea, polybenzoguanamine, polyfuran, polyxylene, phenol resins, polysaccharides and silica. By encapsulating fluorescent dyes into such a particle, a fluorescent dye-containing nanoparticle in which deterioration caused by irradiation with an excitation light is less likely to occur as compared to a case where the fluorescent dyes are used by themselves (high light resistance) and the brightness retention rate of an immunostained part can be adjusted in a range of 80% to 120% in relation to the brightness retention rate of a part stained for morphological observation can be produced. For example, hydrophobic compounds such as polystyrene, polymelamine and silica are preferred as the parent material of a highly light-resistant, fluorescent dye-containing nanoparticle.

Meanwhile, it is preferred that the fluorescent dyes to be encapsulated be those which are excited in a wavelength range of 350 to 450 nm or in a long wavelength range of 550 nm or longer such that their excitation wavelengths do not overlap with the absorption wavelength of eosin, which is a representative staining agent for morphological observation.

Such fluorescent dyes can be selected from, for example, rhodamine-based dye molecules, squarylium-based dye molecules, cyanine-based dye molecules, aromatic ring-based dye molecules, oxazine-based dye molecules, carbopyronine-based dye molecules and pyrromethene-based dye molecules. Alternatively, the fluorescent dyes can also be selected from, for example, Alexa Fluor-based dye molecules (registered trademark, manufactured by Invitrogen), BODIPY-based dye molecules (registered trademark, manufactured by Invitrogen), Cy-based dye molecules (registered trademark, manufactured by GE Healthcare), DY-based dye molecules (registered trademark, Dyomics GmbH), HiLyte-based dye molecules (registered trademark, manufactured by AnaSpec Inc.), DyLight-based dye molecules (registered trademark, manufactured by Thermo Fisher Scientific K.K.), ATTO-based dye molecules (registered trademark, manufactured by ATTO-TEC GmbH) and MFP-based dye molecules (registered trademark, manufactured by Mobitec Co., Ltd.). The generic names of these dye molecules are designated based on the main structure (skeleton) or the registered trademark of the respective compounds; therefore, those of ordinary skill in the art can properly understand the scope of fluorescent dyes belonging to the respective generic names without having to bear undue trial and error.

Specific examples of the rhodamine-based dye molecules include 5-carboxy-rhodamine, 6-carboxy-rhodamine, 5,6-dicarboxy-rhodamine, rhodamine 6G, tetramethyl rhodamine, X-rhodamine, Texas Red, Spectrum Red and LD700 PERCHLORATE.

Specific examples of the squarylium-based dye molecules include SRfluor 680-carboxylate, 1,3-Bis[4-(dimethylamino)-2-hydroxyphenyl]-2,4-dihydroxycyclobutenediylium dihydroxide, bis, 1,3-bis[4-(dimethylamino)phenyl]-2,4-dihydroxycyclobutenediylium dihydroxide, bis, 2-(4-(diethylamino)-2-hydroxyphenyl)-4-(4-(diethyliminio)-2-hydroxycyclohexa-2,5-dienylidene)-3-oxocyclobut-1-enolate, 2-(4-(dibutylamino)-2-hydroxyphenyl)-4-(4-(dibutyliminio)-2-hydroxycyclohexa-2,5-dienylidene)-3-oxocyclobut-1-enolate and 2-(8-hydroxy-1,1,7,7-tetramethyl-1,2,3,5,6,7-hexahydropyrido[3,2,1-ij]quinolin-9-yl)-4-(8-hydroxy-1,1,7,7-tetramethyl-2,3,6,7-tetrahydro-1H-pyrido[3,2,1-ij]quinolinium-9(5H)-ylidene)-3-oxocyclobut-1-enolate.

Specific examples of the cyanine-based dye molecules include 1-butyl-2-[5-(1-butyl-1,3-dihydro-3,3-dimethyl-2H-indol-2-ylidene)-penta-1,3-dienyl]-3,3-dimethyl-3eiti-indolium hexafluorophosphate, 1-butyl-2-[5-(1-butyl-3,3-dimethyl-1,3-dihydro-indol-2-ylidene)-3-chloro-penta-1,3-dienyl]-3,3-dimethyl-3H-indolium hexafluorophosphate and 3-ethyl-2-[5-(3-ethyl-3H-benzothiazol-2-ylidene)-penta-1,3-dienyl]-benzothiazol-3-ium iodide.

Specific examples of the aromatic ring-based dye molecules include N,N-bis-(2,6-diisopropylphenyl)-1,6,7,12-(4-tert-butylphenoxy)-perylen-3,4,9,10-tetracarbonacid diimide, N,N'-bis(2,6-diisopropylphenyl)-1,6,7,12-tetraphenoxyperylene-3,4:9,10-tetracarboxdiimide, N,N'-bis(2,6-diisopropylphenyl)perylene-3,4,9,10-bis(dicarbimide), 16,N,N'-bis(2,6-dimethylphenyl)perylene-3,4,9,10-tetracarboxylic diimide, 4,4'-[(8,16-dihydro-8,16-dioxodibenzo[a,j] perylene-2,10-diyl)dioxy]dibutyric acid, 2,10-dihydroxydibenzo[a,j]perylene-8,16-dione, 2,10-bis(3-aminopropoxy) dibenzo[a,j]perylene-8,16-dione, 3,3'-[(8,16-dihydro-8,16-dioxodibenzo[a,j]perylen-2,10-diyl)dioxy]dipropylamine, 17-bis(octyloxy)anthra[9,1,2-cde-]benzo[rst]pentaphene-5-10-dione, octadecanoic acid, 5,10-dihydro-5,10-dioxoanthra [9,1,2-cde]benzo[rst]pentaphene-16,17-diylester and dihydroxydibenzanthrone.

Specific examples of the oxazine-based dye molecules include Cresyl violet, Oxazine 170, EVOblue 30 and Nile Blue.

Specific examples of the carbopyronine-based dye molecules include CARBOPYRONIN 149.

Specific examples of the pyrromethene-based dye molecules include PYRROMETHENE 650.

Specific examples of the Alexa Fluor-based dye molecules include Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700 and Alexa Fluor 750.

Specific examples of the BODIPY-based dye molecules include BODIPY FL, BODIPY TMR, BODIPY 493/503, BODIPY 530/550, BODIPY 558/568, BODIPY 564/570, BODIPY 576/589, BODIPY 581/591, BODIPY 630/650 and BODIPY 650/665 (all of which are manufactured by Invitrogen).

Specific examples of the Cy-based dye molecules include Cy 3.5, Cy 5 and Cy 5.5.

Specific examples of the DY-based dye molecules include DY-590, DY-610, DY-615, DY-630, DY-631, DY-632, DY-633 and DY-634.

Specific examples of the HiLyte-based dye molecules include HiLyte 594 and HiLyteFluor TR.

Specific examples of the DyLight-based dye molecules include DyLight 594 and DyLight 633.

Specific examples of the ATTO-based dye molecules include ATTO 590, ATTO 610, ATTO 620, ATTO 633 and ATTO 655.

Specific examples of the MFP-based dye molecules include MFP 590 and MFP 631.

Examples of other dye include C-phycocyanin, phycocyanin, APC (allophycocyanin), APC-XL and NorthernLights 637.

Further, examples of dyes also include derivatives of the above-described dyes (those which can function as a fluorescent dye, such as known derivatives).

In the fluorescent dye-containing nanoparticle, any one of the above-described fluorescent dyes may be encapsulated individually, or a plurality thereof may be encapsulated in combination.

For example, fluorescent dyes such as aromatic ring-based dye molecules and rhodamine-based dye molecules are preferred because of their relatively high light resistance. Thereamong, perylenes belonging to aromatic ring-based dye molecules, particularly perylene diimide, are preferred. Meanwhile, even when a fluorescent dye having a relatively low light resistance is used, by selecting an appropriate parent material, it is possible to produce a fluorescent dye-containing nanoparticle which satisfies a prescribed brightness retention rate condition of the present invention.

The method of producing a fluorescent dye-containing nanoparticle is not particularly restricted. For introduction of a dye(s) into a particle, any method such as a method of synthesizing a particle by binding a dye molecule to a monomer that is a particle raw material or a method of introducing a dye to a particle by adsorption may be employed.

The average particle diameter of the fluorescent dye-containing nanoparticle is not particularly restricted; however, it is usually 10 to 500 nm, preferably 50 to 200 nm. Further, the variation coefficient which indicates the variation in the particle size is also not particularly restricted; however, it is usually about 20%. Here, the particle size of a fluorescent dye-containing nanoparticle can be determined by taking an electron microscope image thereof using a scanning electron microscope (SEM), measuring the cross-sectional area of the fluorescent dye-containing nanoparticle and then calculating the particle size as the diameter of a circular area corresponding to the measured value. With regard to the average particle size (average particle diameter) and the variation coefficient of a group of fluorescent dye-containing nanoparticles, after measuring the particle sizes (particle diameters) of a sufficient number (for example, 1,000) of fluorescent dye-containing nanoparticles in the above-described manner, the average particle size is calculated as the arithmetic mean of the measured values and the variation coefficient is calculated by the following equation: 100×standard deviation of particle size/average particle size.

[Step of Staining for Morphological Observation]

In the step of staining for morphological observation, particularly when the morphology of a tissue sample is observed, the above-described hematoxylin-eosin staining (HE staining) using two dyes, hematoxylin and eosin, is typically used; however, in the present invention, the staining for morphological observation is not restricted thereto. Examples of other staining for morphological observation include Papanicolaou staining (Pap staining) used for cytological diagnosis.

In HE staining, hematoxylin stains cell nuclei, calcareous parts, cartilaginous tissues, bacteria and mucus in livid to light blue and eosin stains cytoplasm, interstitial tissues, various fibers, erythrocytes and keratinocyte in red to dark red. In other staining for morphological observation, cell nuclei, calcareous parts, cartilaginous tissues, bacteria and mucus may be stained in livid to light blue with a hematoxylin analogue or a dye having an absorption wavelength similar to that of hematoxylin, and cytoplasm, interstitial tissues, various fibers, erythrocytes and keratinocyte may be stained in red to dark red with an eosin analogue or a dye having absorption and emission wavelengths similar to those of eosin.

[Immunostaining Step]

In the present invention, as an immunostaining method, a fluorescent staining method in which a biological substance to be detected is stained with the above-described fluorescent label for immunostaining is employed.

For example, when immunostaining a specific antigen, a method in which a label (conjugate) is prepared by directly binding a fluorescent label and a primary antibody and an antigen is then stained (primary antibody method), a method in which a label is prepared by directly binding a fluorescent label and a secondary antibody and an antigen bound with a primary antibody is then stained (secondary antibody method) or a method in which a label is prepared by directly binding a fluorescent label and biotin and an antigen bound with a primary antibody and avidin or a streptavidin-modified secondary antibody is then stained (biotin-avidin method or sandwich method) can be used.

Any primary antibody may be used in the immunostaining and the primary antibody is variable depending on the subject to be immunostained. For example, when immunostaining is performed using HER2 as an antigen, an anti-HER2 antibody is used. In addition, any secondary antibody may be used and the secondary antibody is variable depending on the primary antibody. Examples of secondary antibody include anti-mouse, rabbit, bovine, goat, sheep, dog and chicken antibodies.

For binding of a fluorescent label with an antibody or biotin, any existing method may be used. For example, amidation by reaction between amine and carboxylic acid, sulfidation by reaction between maleimide and thiol, imination by reaction between aldehyde and amine, or amination by reaction between epoxy and amine can be used.

The above-described immunostaining is not restricted to tissue staining, and cell staining can be also applied. Further, the biological substance to be detected is not particularly restricted as long as there is a substance which specifically binds thereto. Typically, a combination of an antigen and an antibody is used as described above; however, it is also possible to use, for example, a combination of a nucleic acid molecule (oligonucleotide or polynucleotide) and a nucleic acid molecule having a sequence hybridizable thereto.

[Fluorescence Observation Step]

By irradiating the pathological specimen subjected to immunostaining and staining for morphological observation in the above-described steps with an excitation light having a wavelength appropriate for the fluorescent label used, the fluorescence emitted by the fluorescent label is observed. By this step, a prescribed biomolecule existing in the pathological specimen can be detected and this information can be utilized to determine the appropriateness of applying an antibody pharmaceutical (such as Herceptin which targets HER2).

For the irradiation of an excitation light, the same irradiation means as the one used in an ordinary fluorescence observation may be employed. For example, from a laser light source installed in a fluorescence microscope, an excitation light having an appropriate wavelength and output may be irradiated to the stained pathological specimen using, as required, a filter which selectively allows a light of a prescribed wavelength to pass therethrough.

Observation of fluorescence may be performed either through the lens barrel of a fluorescence microscope or on a separate display means (such as a monitor) showing an image taken by a camera mounted on a fluorescence microscope. Though depending on the fluorescent substance, even when the fluorescence cannot be sufficiently observed visually through the lens barrel of a fluorescence microscope, the fluorescence may be observed by taking an image thereof with a camera in some cases. As required, a filter which selectively allows a light of a prescribed wavelength to pass therethrough may also be used.

In the present invention, immunostaining and staining for morphological observation are both performed on the same pathological specimen; however, for observation of an image produced by the staining for morphological observation, it is not required to irradiate the pathological specimen with an excitation light for exciting the fluorescent label used in the immunostaining and the image may be observed under the same observation conditions as those of a light microscope.

In the biological substance detection method according to the present invention, since the brightness retention rate of an immunostained part is in a specific range of ratio with respect to the brightness retention rate of a part stained for morphological observation, there is no adverse effect on the assessment of the immunostaining results. Therefore, the fluorescence observation can be performed after irradiating an excitation light for an arbitrary time; however, the fluorescence observation is performed preferably within 90 minutes after initiating the irradiation of an excitation light, more preferably within 30 minutes after initiating the irradiation of an excitation light, under normal irradiation conditions (such as irradiation energy).

In the present invention, the ratio (RS/RN) of the brightness retention rate of an immunostained part (RS) to the brightness retention rate of a part stained for morphological observation (RN) is set to be in a range of 80 to 120%, preferably 100 to 120%. When the above-described ratio is lower than 80%, the brightness of the immunostained part becomes excessively low relative to that of the part stained for morphological observation at the time of fluorescence observation, while when the above-described ratio is higher than 120%, the brightness of the part stained for morphological observation becomes excessively low relative to that of the immunostained part at the time of fluorescence observation. In both of these cases, the information obtained from the stained pathological specimen may be largely degraded by irradiation with an excitation light.

Here, the brightness of an immunostained part (S) is a value obtained as an average brightness of the sites stained with a fluorescent label for immunostaining. Further, the brightness retention rate of an immunostained part (RS) is a value which is calculated by an equation, $S_A/S_B$, from the brightness measured before irradiating an excitation light for fluorescence observation ($S_B$) and the brightness measured at the time of observing the fluorescence emitted by the fluorescent label after irradiating an excitation light for a certain period of time ($S_A$).

Meanwhile, the brightness of a part stained for morphological observation (N) is a value obtained as an average brightness of the sites that are not stained with a fluorescent label for immunostaining but with a staining agent for morphological observation. Further, the brightness retention rate of a part stained for morphological observation (RN) is a value which is calculated by an equation, $N_A/N_B$, from the brightness measured before irradiating an excitation light for fluorescence observation ($N_B$) and the brightness measured at the time of observing the fluorescence emitted by the fluorescent label after irradiating an excitation light for a certain period of time ($N_A$).

The brightness of an immunostained part (S) and that of a part stained for morphological observation (N) can be determined by, for example, taking an image using a camera mounted on a fluorescence microscope and then calculating the brightness of each pixel within a prescribed area of the image using an image analysis software.

In the fluorescence observation, for example, the ratio of the brightness retention rates (RS/RN) may be calculated in the above-described manner for a test sample under certain staining conditions (combination of a staining agent for morphological observation and a fluorescent label for immunostaining) and excitation light irradiation conditions (e.g., wavelength and intensity). If the above-described ratio was confirmed to be in a range of 80 to 120%, the biological substance detection method can be carried out with a certain level of reliability by observing the fluorescence for other pathological specimen under the same staining and excitation light irradiation conditions as those used for the test sample. Further, if the above-described ratio was found to be outside the range of 80 to 120%, the observation of fluorescence for other pathological specimen can be performed after changing the staining and excitation light irradiation conditions to adjust the ratio to be in a range of 80 to 120%.

Alternatively, when the ratio of the brightness retention rates (RS/RN) under particular staining and excitation light irradiation conditions was once confirmed to be in a range of 80 to 120% as described above, as long as the same combination and observation conditions are applied, the biological substance detection method can be assumed to have a certain level of reliability and thus be operated without verifying it using the test sample for every observation.

EXAMPLES

The present invention will now be described in detail by way of examples thereof; however, the present invention is not restricted to the following examples.

Sample Preparation

Sample 1-1

Texas Red-Containing Silica Particle

In DMF, 3.4 mg of a fluorescent dye, Sulforhodamine 101 acid chloride (manufactured by Dojinsha Co., Ltd., Texas Red dye), and 3 μL of 3-aminopropyltrimethoxysilane (manufactured by Shin-Etsu Chemical Co., Ltd., KBM903) were mixed to obtain an organoalkoxysilane compound. Then, 0.6 mL of the thus obtained organoalkoxysilane compound was mixed for 3 hours with 48 mL of ethanol, 0.6 mL of TEOS (tetraethoxysilane), 2 mL of water and 2 mL of 28% aqueous ammonia. The mixture produced in the above-described step was centrifuged at 10,000 G for 20 minutes and the resulting supernatant was removed. Then, ethanol was added to disperse the precipitates and the resultant was centrifuged again. The precipitates were washed twice with each of ethanol and pure water by the same procedure. By SEM observation of the thus obtained tetramethyl rhodamine-containing silica nanoparticles, the average particle size and the variation coefficient were found to be 104 nm and 12%, respectively.

The thus obtained fluorescent substance-containing silica nanoparticles were adjusted with PBS (phosphate-buffered physiological saline) containing 2 mM of EDTA (ethylenediamine tetraacetic acid) to a concentration of 3 nM. This solution was then mixed with SM(PEG)12 (manufactured by Thermo Fisher Scientific K.K., succinimidyl-[(N-maleimidopropionamido)-dodecaethylene glycol]ester) to a final concentration of 10 mM and allowed to react for 1 hour. The thus obtained mixture was centrifuged at 10,000 G for 20 minutes and the resulting supernatant was removed. Then, PBS containing 2 mM of EDTA was added to disperse the precipitates and the resultant was centrifuged again. The precipitates were washed three times by the same procedure to obtain fluorescent dye-containing particles for antibody binding.

On another front, anti-human HER 2 antibodies were subjected to a reduction treatment with 1M dithiothreitol (DTT) and excess DTT was then removed using a gel filtration column, thereby obtaining a solution of reduced antibodies capable of binding to silica particles.

The thus obtained fluorescent dye-containing particles for antibody binding and reduced antibodies were mixed in PBS containing 2 mM of EDTA and allowed to react for 1 hour. Thereafter, the reaction was terminated with an addition of 10 mM mercaptoethanol. The thus obtained solution was centrifuged at 10,000 G for 20 minutes and the resulting supernatant was removed. Then, PBS containing 2 mM of EDTA was added to disperse the precipitates and the resultant was centrifuged again. The precipitates were washed three times by the same procedure to obtain fluorescent dye-containing particles bound with anti-human ER antibody.

Sample 1-2

ATTO 590-Containing Silica Particle

Fluorescent dye-containing particles bound with anti-human HER2 antibody were synthesized in the same manner as the sample 1-1, except that ATTO 590 dye (manufactured by ATTO-TEC GmbH) was used as the fluorescent dye.

Sample 1-3

Cresyl Violet-Containing Silica Particle

Fluorescent dye-containing particles bound with anti-human HER2 antibody were synthesized in the same manner as the sample 1-1, except that Cresyl Violet (manufactured by Sigma-Aldrich) was used as the fluorescent dye and 3-glycidyloxypropyltrimethoxysilane (manufactured by TCI Co., Ltd.) was used in place of 3-aminopropyltrimethoxysilane (manufactured by Shin-Etsu Chemical Co., Ltd., KBM903).

Sample 1-4

Perylene Diimide-Containing Silica Particle

Perylene diimide, which was used as a fluorescent dye, was prepared by the following method. N,N'-bis(2,6-diisopropylphenyl)-1,6,7,12-tetraphenoxyperylene-3,4:9,10-tetracarboxdiimide was treated with concentrated sulfuric acid to prepare a perylene diimide sulfonic acid derivative. This was then converted to an acid chloride to obtain a perylene diimide sulfonic acid chloride derivative. Fluorescent dye-containing particles bound with anti-human HER2 antibody were synthesized in the same manner as the sample 1-1, except that the thus obtained perylene diimide sulfonic acid chloride derivative was used as the fluorescent dye.

Sample 1-5

Texas Red-Containing Melamine Particle

After adding 2.5 mg Sulforhodamine 101 (manufactured by Sigma-Aldrich) to 22.5 mL of water, the resultant was heated at 70° C. for 20 minutes on a hot stirrer, followed by an addition of 1.5 g of water-soluble melamine resin "Nikalac MX-035" (manufactured by Nippon Carbide Industries Co., Ltd.) and heating with stirring for another 5 minutes. Then, 100 µL of formic acid was added and the resultant was heated with stirring for 20 minutes at 60° C. and subsequently cooled to room temperature. Thereafter, the resulting reaction mixture was placed in a centrifugal tube and centrifuged using a centrifuge at 12,000 rpm for 20 minutes, followed by removal of the resulting supernatant. The precipitates were washed with ethanol and water. After modifying the thus obtained particles with SM (PEG) 12 (manufactured by Thermo Fisher Scientific K.K., succinimidyl-[(N-maleimidopropionamido)-dodecaethylene glycol]ester) in the same manner as in the case of the sample 1-1, fluorescent dye-containing particles bound with anti-human HER2 antibody were synthesized.

Sample 1-6

ATTO 590-Containing Melamine Particle

Fluorescent dye-containing particles bound with anti-human HER2 antibody were synthesized in the same manner as the sample 1-5, except that ATTO 590 (manufactured by ATTO-TEC GmbH) was used as the fluorescent dye.

Sample 1-7

Perylene Diimide-Containing Melamine Particle

Fluorescent dye-containing particles bound with anti-human HER2 antibody were synthesized in the same manner as the sample 1-5, except that a perylene diimide sulfonic acid derivative was used as the fluorescent dye.

Sample 1-8

Texas Red-Containing Cross-Linked PS Particle

Texas Red dye-containing cross-linked PS particles were prepared by a soap-free emulsion polymerization method. A fluorescent dye, Sulforhodamine 101 acid chloride (manufactured by Dojinsha Co., Ltd., Texas Red dye), was mixed with 4-aminostyrene (manufactured by Tokyo Chemical Industry Co., Ltd.) at room temperature for 1 hour to prepare dye-bound styrene. To 5 mL of pure water aerated by argon bubbling, 0.18 g of glycidyl methacrylate (manufactured by Tokyo Chemical Industry Co., Ltd.), 0.05 g of styrene (manufactured by Wako Pure Chemical Industries, Ltd.), 0.05 g of divinylbenzene and 0.005 g of the thus obtained dye-bound styrene were added. After heating the resultant with stirring to 70° C., 0.012 g of a water-soluble azo polymerization initiator, V-50 (manufactured by Wako Pure Chemical Industries, Ltd.), was added and the resulting mixture was allowed to react for 12 hours. The resulting reaction solution was centrifuged at 10,000 G for 20 minutes to recover particles. The recovered particles were purified by dispersing them in pure water and then centrifuging the resulting dispersion once again for recovery. The thus obtained particles were added to an excess amount of aqueous ammonia so as to convert the epoxy groups at the particle terminals into amino groups. After modifying the resulting particles with SM(PEG)12 (manufactured by Thermo Fisher Scientific K.K., succinimidyl-[(N-maleimidopropionamido)-dodecaethylene glycol] ester) in the same manner as in the case of the sample 1-1, fluorescent dye-containing particles bound with anti-human HER2 antibody were synthesized.

Sample 1-9

ATTO 590-Containing Cross-Linked PS Particle

Fluorescent dye-containing particles bound with anti-human HER2 antibody were synthesized in the same manner as the sample 1-8, except that ATTO 590 (manufactured by ATTO-TEC GmbH) was used as the fluorescent dye.

Sample 1-10

Cresyl Violet-Containing Cross-Linked PS Particle

Fluorescent dye-containing particles bound with anti-human HER2 antibody were synthesized in the same manner as the sample 1-8, except that Cresyl Violet (manufactured by Sigma-Aldrich) was used as the fluorescent dye.

Sample 1-11

Perylene Diimide-Containing Cross-Linked PS Particle

Fluorescent dye-containing particles bound with anti-human HER2 antibody were synthesized in the same manner as the sample 1-8, except that a perylene diimide sulfonic acid derivative converted into an acid chloride was used as the fluorescent dye.

Sample 2-1

Cy 3.5-Containing Silica Particle

Fluorescent dye-containing particles bound with anti-human HER2 antibody were synthesized in the same manner as the sample 1-1, except that Cy-3.5 SE (manufactured by Roche) was used as the fluorescent dye.

Sample 2-2

Cy 3.5-Containing Melamine Particle

Fluorescent dye-containing particles bound with anti-human HER2 antibody were synthesized in the same manner as the sample 1-5, except that Cy-3.5 SE (manufactured by Roche) was used as the fluorescent dye.

Sample 2-3

BODIPY TR-Containing Silica Particle

Fluorescent dye-containing particles bound with anti-human HER2 antibody were synthesized in the same manner as the sample 1-1, except that BODIPY TR (manufactured by Invitrogen) was used as the fluorescent dye.

Sample 2-4

BODIPY TR-Containing Melamine Particle

Fluorescent dye-containing particles bound with anti-human HER2 antibody were synthesized in the same manner as the sample 1-5, except that BODIPY TR (manufactured by Invitrogen) was used as the fluorescent dye.

[Evaluation by Tissue Staining]

Using the samples 1-1 to 1-11 and 2-1 to 2-4, immunostaining and staining for morphological observation (HE staining) were performed on human breast tissue. The samples 1-1 to 1-11 correspond to Examples 1 to 11 and the samples 2-1 to 2-4 correspond to Comparative Examples 1 to 4.

As a section to be stained, a tissue array slide manufactured by Cosmo Bio Co., Ltd. (CB-A712) was used. After subjecting the tissue array slide to a deparaffinization treatment, an antigen inactivation treatment was performed by subjecting the tissue array slide to displacement washing with water and a 15-minute autoclave treatment in 10 mM citrate buffer (pH 6.0). After the antigen inactivation treatment, the tissue array slide was washed with a PBS buffer and then subjected to a blocking treatment with a 1% BSA-containing PBS buffer for 1 hour in a moist chamber. Thereafter, the tissue section was allowed to react for 3 hours with each of the samples 1-1 to 1-11 and 2-1 to 2-4 that were diluted with a 1% BSA-containing PBS buffer to a concentration of 0.05 nM. After the reaction with each of the samples 1-1 to 1-11 and 2-1 to 2-4, the resulting tissue array slide was washed with a PBS buffer.

After the immunostaining, staining for morphological observation (HE staining) was performed. The immunostained section was stained with hematoxylin for 5 minutes in Mayer's hematoxylin solution and then washed with running water (about 45° C.) for 3 minutes. Then, after staining the section with eosin for 5 minutes in a 1% eosin solution, an operation of immersing the resulting section in pure ethanol for 5 minutes was repeated four times to perform washing and dehydration. Subsequently, an operation of immersing the section in xylene for 5 minutes was repeated four times to perform clearing. Lastly, the section was sealed with a sealant, Entellan New (manufactured by Merck KGaA), thereby obtaining a sample slide for observation.

The respective tissue sections that were immunostained with the samples 1-1 to 1-11 and 2-1 to 2-4 and then stained for morphological observation were allowed to emit fluorescence by irradiation with an excitation light. Then, using an inverted fluorescence microscope (manufactured by Carl Zeiss), images were obtained from the respective tissue sections.

Using an optical filter, the excitation and fluorescence wavelengths (nm) were set to be 575 to 600 nm and 612 to 682 nm, respectively (Tables 1 and 2 show the maximum absorption and maximum emission wavelengths of the particles). The conditions of the excitation wavelength in the microscope observation and image acquisition were set such that the irradiation energy around the center of the field of view became 900 W/cm$^2$ for 580-nm excitation and 500 W/cm$^2$ for 365-nm excitation. In the image acquisition, the exposure time was arbitrarily set such that the image brightness was not saturated. The measurements were performed at an exposure time of, for example, 4,000 μs.

The brightness of each pixel was calculated from the thus obtained respective images using an image analysis software, Image-J, and the average brightness of the sites that were stained with each fluorescent label of the samples 1-1 to 1-11 and 2-1 to 2-4 (immunostained part) was calculated (brightness of the immunostained part). This average brightness corresponds to a signal value (S). A brightness of "0" was defined as black (darkest) and a brightness of "255" was defined as white (brightest). At the same time, the average brightness of the sites that were not stained with the fluorescent label but with eosin in the vicinity of the fluorescently-labeled cells (part stained for morphological observation) was also calculated (brightness of the part stained for morphological observation). This average brightness corresponds to a noise value (N). The ratio of the brightness of immunostained part and that of part stained for morphological observation was defined as "S/N ratio".

Decoloration of the immunostained part and the part stained for morphological observation was evaluated by continuing irradiation of an excitation light with the field of view being fixed for 30 minutes, determining the brightness of the immunostained part and that of the part stained for immunological observation from both microscope images that were taken prior to the irradiation (at the beginning of the irradiation, 0 minute) and after the irradiation (30 minutes), and then calculating the brightness retention rate, which is represented by an equation: (brightness after 30-minute irradiation/brightness immediately after the initiation of irradiation), for both of the immunostained part and the part stained for immunological observation. In addition, the pre-irradiation and post-irradiation S/N ratios were calculated to determine the rate of change in the S/N ratio before and after the irradiation, which is represented by an equation: (post-irradiation S/N ratio–pre-irradiation S/N ratio)/pre-irradiation S/N ratio. This value was used as an index of the difference in the appearance before and after the irradiation with an excitation light.

Further, a serial section composed of the sections simultaneously subjected to the above-described immunostaining and staining for morphological observation was stained with DAB to set in advance a region in which the expression of HER2 on cell membrane was limited (1+). A region corresponding thereto of a section simultaneously subjected to immunostaining and staining for morphological observation was visually evaluated before and after the irradiation under a fluorescence microscope. When the evaluation did not change before and after the irradiation, the section was assigned with "o", and when the evaluation changed before and after the irradiation, the section was assigned with "×".

TABLE 1

|  | Example 1 | | Example 2 | | Example 3 | | Example 4 | | Example 5 | |
| --- | --- | --- | --- | --- | --- | --- | --- | --- | --- | --- |
|  | 0 min. | 30 min. | 0 min. | 30 min. | 0 min. | 30 min. | 0 min. | 30 min. | 0 min. | 30 min. |
| Dye | Texas Red | | ATTO590 | | Cresyl violet | | Perylene | | Texas Red | |
| Parent material | Silica | | Silica | | Silica | | Silica | | Melamine | |
| Maximum absorption wavelength (nm) | 585 | | 594 | | 600 | | 580 | | 590 | |

TABLE 1-continued

| | | | | | | | | | | |
|---|---|---|---|---|---|---|---|---|---|---|
| Maximum emission wavelength (nm) | 613 | | 624 | | 620 | | 620 | | 612 | |
| Brightness of eosin-stained part | 20 | 16 | 20 | 16 | 20 | 16 | 20 | 16 | 20 | 16 |
| Brightness of fluorescently-stained part | 80 | 59 | 80 | 60 | 80 | 52 | 80 | 71 | 80 | 58 |
| S/N ratio | 4.0 | 3.7 | 4.0 | 3.8 | 4.0 | 3.3 | 4.0 | 4.4 | 4.0 | 3.6 |
| Rate of change in S/N ratio before and after irradiation (%) | −8 | | −5 | | −18 | | 10 | | −10 | |
| Brightness retention rate of eosin-stained part after 30 minutes in relation to the brightness at 0 minute (%) | 80 | | 80 | | 80 | | 80 | | 80 | |
| Brightness retention rate of fluorescently-stained part after 30 minutes in relation to the brightness at 0 minute (%) | 74 | | 75 | | 66 | | 89 | | 73 | |
| Ratio of the brightness retention rate of fluorescently-stained part to the brightness retention rate of eosin-stained part (%) | 92 | | 94 | | 82 | | 111 | | 91 | |
| Concordance between the visual evaluation results obtained at 0 and 30 minutes | ◯ | | ◯ | | ◯ | | ◯ | | ◯ | |

| | Example 6 | | Example 7 | | Example 8 | | Example 9 | | Example 10 | | Example 11 | |
|---|---|---|---|---|---|---|---|---|---|---|---|---|
| | 0 min. | 30 min. | 0 min. | 30 min. | 0 min. | 30 min. | 0 min. | 30 min. | 0 min. | 30 min. | 0 min. | 30 min. |
| Dye | ATTO590 | | Perylene | | Texas Red | | ATTO590 | | Cresyl Violet | | Perylene | |
| Parent material | Melamine | | Melamine | | Cross-linked PS | | Cross-linked PS | | Cross-linked PS | | Cross-linked PS | |
| Maximum absorption wavelength (nm) | 595 | | 580 | | 580 | | 594 | | 600 | | 580 | |
| Maximum emission wavelength (nm) | 624 | | 625 | | 615 | | 624 | | 620 | | 620 | |
| Brightness of eosin-stained part | 20 | 16 | 20 | 16 | 20 | 16 | 20 | 16 | 20 | 16 | 20 | 16 |
| Brightness of fluorescently-stained part | 80 | 58 | 80 | 72 | 80 | 64 | 80 | 68 | 80 | 67 | 80 | 77 |
| S/N ratio | 4.0 | 3.6 | 4.0 | 4.5 | 4.0 | 4.0 | 4.0 | 4.2 | 4.0 | 4.2 | 4.0 | 4.8 |
| Rate of change in S/N ratio before and after irradiation (%) | −10 | | 13 | | 0 | | 5 | | 5 | | 20 | |
| Brightness retention rate of eosin-stained part after 30 minutes in relation to the brightness at 0 minute (%) | 80 | | 80 | | 80 | | 80 | | 80 | | 80 | |
| Brightness retention rate of fluorescently-stained part after 30 minutes in relation to the brightness at 0 minute (%) | 72 | | 90 | | 80 | | 85 | | 83 | | 96 | |
| Ratio of the brightness retention rate of fluorescently-stained part to the brightness retention rate of eosin-stained part (%) | 90 | | 112 | | 100 | | 106 | | 104 | | 120 | |
| Concordance between the visual evaluation results obtained at 0 and 30 minutes | ◯ | | ◯ | | ◯ | | ◯ | | ◯ | | ◯ | |

| | Comparative Example 1 | | Comparative Example 2 | | Comparative Example 3 | | Comparative Example 4 | |
|---|---|---|---|---|---|---|---|---|
| | 0 min. | 30 min. | 0 min. | 30 min. | 0 min. | 30 min. | 0 min. | 30 min. |
| Dye | cy3.5 | | cy3.5 | | BODIPY TR | | BODIPY TR | |
| Parent material | Silica | | Melamine | | Silica | | Melamine | |
| Maximum absorption wavelength (nm) | 581 | | 590 | | 588 | | 592 | |
| Maximum emission wavelength (nm) | 596 | | 608 | | 616 | | 620 | |
| Brightness of eosin-stained part | 20 | 16 | 20 | 16 | 20 | 16 | 20 | 16 |
| Brightness of fluorescently-stained part | 80 | 44 | 80 | 42 | 80 | 49 | 80 | 47 |

TABLE 1-continued

| | | | | | | | | |
|---|---|---|---|---|---|---|---|---|
| S/N ratio | 4.0 | 2.7 | 4.0 | 2.6 | 4.0 | 3.1 | 4.0 | 3.0 |
| Rate of change in S/N ratio before and after irradiation (%) | | −33 | | −35 | | −23 | | −25 |
| Brightness retention rate of eosin-stained part after 30 minutes in relation to the brightness at 0 minute (%) | | 80 | | 80 | | 80 | | 80 |
| Brightness retention rate of fluorescently-stained part after 30 minutes in relation to the brightness at 0 minute (%) | | 54 | | 53 | | 62 | | 59 |
| Ratio of the brightness retention rate of fluorescently-stained part to the brightness retention rate of eosin-stained part (%) | | 68 | | 66 | | 77 | | 74 |
| Concordance between the visual evaluation results obtained at 0 and 30 minutes | | x | | x | | x | | x |

Figure 2:
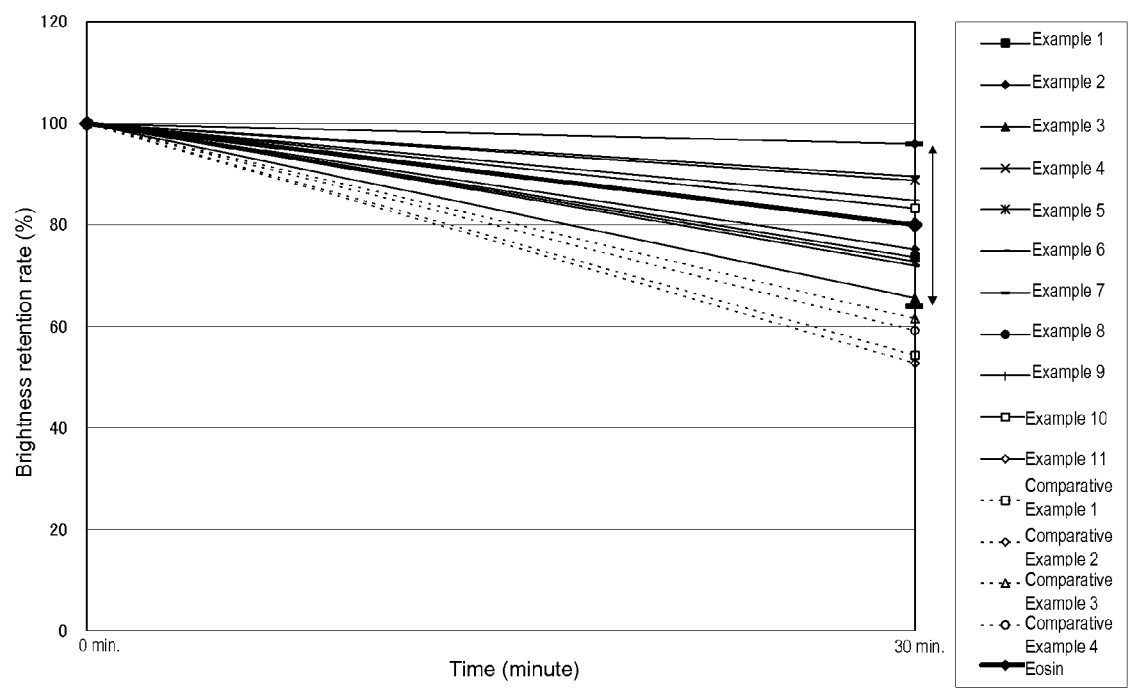
FIG. 2 is a graph showing the brightness retention rate of an eosin part (80% in all cases) and that of the respective labeled parts in Examples 1 to 11 (samples 1-1 to 1-11) and Comparative Examples 1 to 4 (samples 2-1 to 2-4).

In Table 1 and FIG. 2, Examples 1 to 11 correspond to the samples 1-1 to 1-11 and Comparative Examples 1 to 4 correspond to the samples 2-1 to 2-4. In each of Examples and Comparative Examples, the dye and parent material of the particles were different and the rate of the brightness change after the irradiation with an excitation light was also different. Consequently, the S/N ratio, which is the ratio of the brightness of the immunostained part in relation to that of the part stained for morphological observation, also changed before and after the irradiation with an excitation light. In Examples where the brightness retention rate of the immunostained part was in a range of 80 to 120% in relation to the brightness retention rate of the part stained for morphological observation, the region in which the expression of HER2 on cell membrane was limited (1+) was given the same evaluation before and after the irradiation with an excitation light and the results show that there was no profound effect on the appearance of the observation samples. On the other hand, in Comparative Examples where the brightness retention rate of the immunostained part was outside the range of 80 to 120% in relation to the brightness retention rate of the part stained for morphological observation, different evaluations were given before and after the irradiation with an excitation light and the results show that there was an effect on the appearance of the observation samples.

From the above, it is seen that, when staining for morphological observation and immunostaining are simultaneously performed, even if the fluorescent label and/or the staining agent is/are deteriorated, a proper judgment can be made as long as the brightness retention rate of an immunostained part is in a range of 80 to 120% in relation to the brightness retention rate of a part stained for morphological observation when the fluorescent label used in the immunostaining is observed.

The invention claimed is:

1. A fluorescent label comprising:
a nanoparticle containing a parent material and fluorescent dye,
wherein the parent material is a melamine resin or a styrene resin,
the fluorescent dye is a perylene derivative having a sulfonic acid group or a rhodamine derivative having a sulfonic acid group, and
the fluorescent dye is adsorbed to the parent material of the nanoparticle.

2. The fluorescent label according to claim 1, wherein said perylene derivative having a sulfonic acid group is a perylene diimide derivative having a sulfonic acid group.

3. The fluorescent label according to claim 1, wherein said fluorescent dye has a maximum excitation wavelength in a wavelength range of 550 nm to 620 nm and maximum emission wavelength is in a wavelength range of 580 to 700 nm.

4. The fluorescent label according to claim 1, wherein the average particle diameter of said fluorescent dye-containing nanoparticle is 50 to 200 nm.

5. The fluorescent label according to claim 1, wherein said rhodamine derivative having a sulfonic acid group is a sulforhodamine.

\* \* \* \* \*